(12) United States Patent
Parke et al.

(10) Patent No.: US 12,171,631 B2
(45) Date of Patent: Dec. 24, 2024

(54) INTRA-ORAL APPLIANCE

(71) Applicant: Xerosguard Inc., Winnipeg (CA)

(72) Inventors: Gord Parke, Winnipeg (CA); Robert Ward, Calgary (CA)

(73) Assignee: Xerosguard Inc., Winnipeg (CA)

( * ) Notice: Subject to any disclaimer, the term of this patent is extended or adjusted under 35 U.S.C. 154(b) by 220 days.

(21) Appl. No.: 17/548,061

(22) Filed: Dec. 10, 2021

(65) Prior Publication Data
US 2022/0183807 A1    Jun. 16, 2022

Related U.S. Application Data

(60) Provisional application No. 63/124,352, filed on Dec. 11, 2020, provisional application No. 63/238,523, filed on Aug. 30, 2021.

(51) Int. Cl.
*A61C 17/10* (2006.01)

(52) U.S. Cl.
CPC .................................... *A61C 17/10* (2019.05)

(58) Field of Classification Search
CPC .. A61C 5/90; A61C 17/10; A61B 1/24; A61N 2005/1094
See application file for complete search history.

(56) References Cited

U.S. PATENT DOCUMENTS

| | | | | |
|---|---|---|---|---|
| 3,916,880 A * | 11/1975 | Schroer | ................... | A61C 17/10 600/242 |
| 4,019,255 A * | 4/1977 | Cohen | ..................... | A61C 17/10 600/242 |
| 5,037,298 A * | 8/1991 | Hickham | .................. | A61C 5/90 433/93 |
| 5,460,524 A * | 10/1995 | Anderson | ................ | A61B 1/24 433/93 |
| 5,873,718 A * | 2/1999 | Sullivan | ................. | A61C 17/08 433/93 |
| 6,923,761 B1 * | 8/2005 | Dorfman | .................. | A61B 1/24 433/140 |
| 7,785,105 B2 * | 8/2010 | Anderson | .............. | A61C 17/08 433/91 |
| 9,901,332 B2 * | 2/2018 | Jessop | ...................... | A61B 1/32 |
| 10,595,964 B2 | 3/2020 | Chana et al. | | |
| 10,675,126 B2 * | 6/2020 | Bohlman | .................. | A61C 5/90 |
| 2004/0101804 A1 * | 5/2004 | Anderson | .............. | A61C 17/08 433/136 |
| 2007/0218422 A1 * | 9/2007 | Ehrenfeld | ................ | A61C 5/90 433/140 |
| 2020/0375696 A1 * | 12/2020 | Jessop | ...................... | A61B 1/24 |
| 2022/0218454 A1 * | 7/2022 | Eldib | ..................... | A61C 17/10 |

* cited by examiner

*Primary Examiner* — Ralph A Lewis
(74) *Attorney, Agent, or Firm* — Standley Law Group LLP; Beverly A. Marsh; Kenny W. Pung

(57) ABSTRACT

An intra-oral appliance, an internal member and an external member is provided. The internal member can include a tongue crib, a poseable first arm connected at a first end to the back end of the tongue crib, and a poseable second arm connected at a first end to the back end of the tongue crib. The poseable first arm and the poseable second allow the tongue crib to be moved into a position and held in the position. The external member can include a first lip retractor, a second lip retractor, a first retractor flange, a second retractor flange and connectors attachable to the first arm and the second arm of the internal member.

11 Claims, 20 Drawing Sheets

INTRA-ORAL APPLIANCE

CROSS-REFERENCE TO RELATED APPLICATIONS

This application claims the benefit of U.S. Provisional Application No. 63/124,352, filed Dec. 11, 2020 and U.S. Provisional Application No. 63/238,523, filed Aug. 30, 2021, the disclosures of each of which are hereby incorporated by reference as if fully restated herein.

TECHNICAL FIELD

The present invention relates to dental appliance and more particularly an intra-oral appliance for providing isolation and moisture control of teeth by tongue and mucosa retraction.

BACKGROUND

Intra-oral isolation, the separation of a patient's teeth from his or her tongue and mucosa is required during many if not most dental procedures. However, it is especially important in procedures the involve adhesives and bonding of material to the teeth. However, there are a number of challenges with a patient's mouth and isolating the tongue and mucosa.

SUMMARY OF THE INVENTION

In an aspect, an internal member for an intra-oral appliance is provided. The internal member can include a tongue crib defining an interior space sized to accept a tongue of a patient, the tongue crib having an opening in a back end of the tongue crib leading into the interior space, a poseable first arm connected at a first end to the back end of the tongue crib, and a poseable second arm connected at a first end to the back end of the tongue crib. The poseable first arm and the poseable second allow the tongue crib to be moved into a position and held in the position.

In another aspect, an external member for an intra-oral appliance is provided. The external member can have a first lip retractor having a generally arcuate shape, an inner surface, and an outer surface having an open channel with a substantially semi-circular cross-section, a second lip retractor having a generally arcuate shape, an inner surface, and an outer surface having an open channel with a substantially semi-circular cross-section, a first retractor flange connected to the first lip retractor at a front end of the first lip retractor and extending outwards from the outer surface of the first lip retractor, a second retractor flange connected to the second lip retractor at a front end of the second lip retractor and extending outwards from the outer surface of the second lip retractor, a first wing member attached to the first lip retractor and extending backwards from the inner surface of the lip retractor, a second wing member attached to the second lip retractor and extending backwards from the inner surface of the second lip retractor, a flexible resilient member connected between the first retractor flange and the second retractor flange, the flexible resilient member biasing the first lip retractor and the second lip retractor apart, and connectors attachable to a first arm and a second arm of an internal member.

In another aspect, an intra-oral appliance comprising an internal member and an external member is provided. The internal member can include a tongue crib defining an interior space sized to accept a tongue of a patient, the tongue crib having an opening in a back end of the tongue crib leading into the interior space, a poseable first arm connected at a first end to the back end of the tongue crib, and a poseable second arm connected at a first end to the back end of the tongue crib. The poseable first arm and the poseable second allow the tongue crib to be moved into a position and held in the position, The an external member can include a first lip retractor having a generally arcuate shape, an inner surface, and an outer surface having an open channel with a substantially semi-circular cross-section, a second lip retractor having a generally arcuate shape, an inner surface, and an outer surface having an open channel with a substantially semi-circular cross-section, a first retractor flange connected to the first lip retractor at a front end of the first lip retractor and extending outwards from the outer surface of the first lip retractor, a second retractor flange connected to the second lip retractor at a front end of the second lip retractor and extending outwards from the outer surface of the second lip retractor, a first wing member attached to the first lip retractor and extending backwards from the inner surface of the lip retractor, a second wing member attached to the second lip retractor and extending backwards from the inner surface of the second lip retractor, a flexible resilient member connected between the first retractor flange and the second retractor flange, the flexible resilient member biasing the first lip retractor and the second lip retractor apart, and connectors attachable to the first arm and the second arm of the internal member.

BRIEF DESCRIPTION OF THE DRAWINGS

A preferred embodiment of the present invention is described below with reference to the accompanying drawings, in which.

DETAILED DESCRIPTION OF THE ILLUSTRATED EMBODIMENTS

Figure 1:
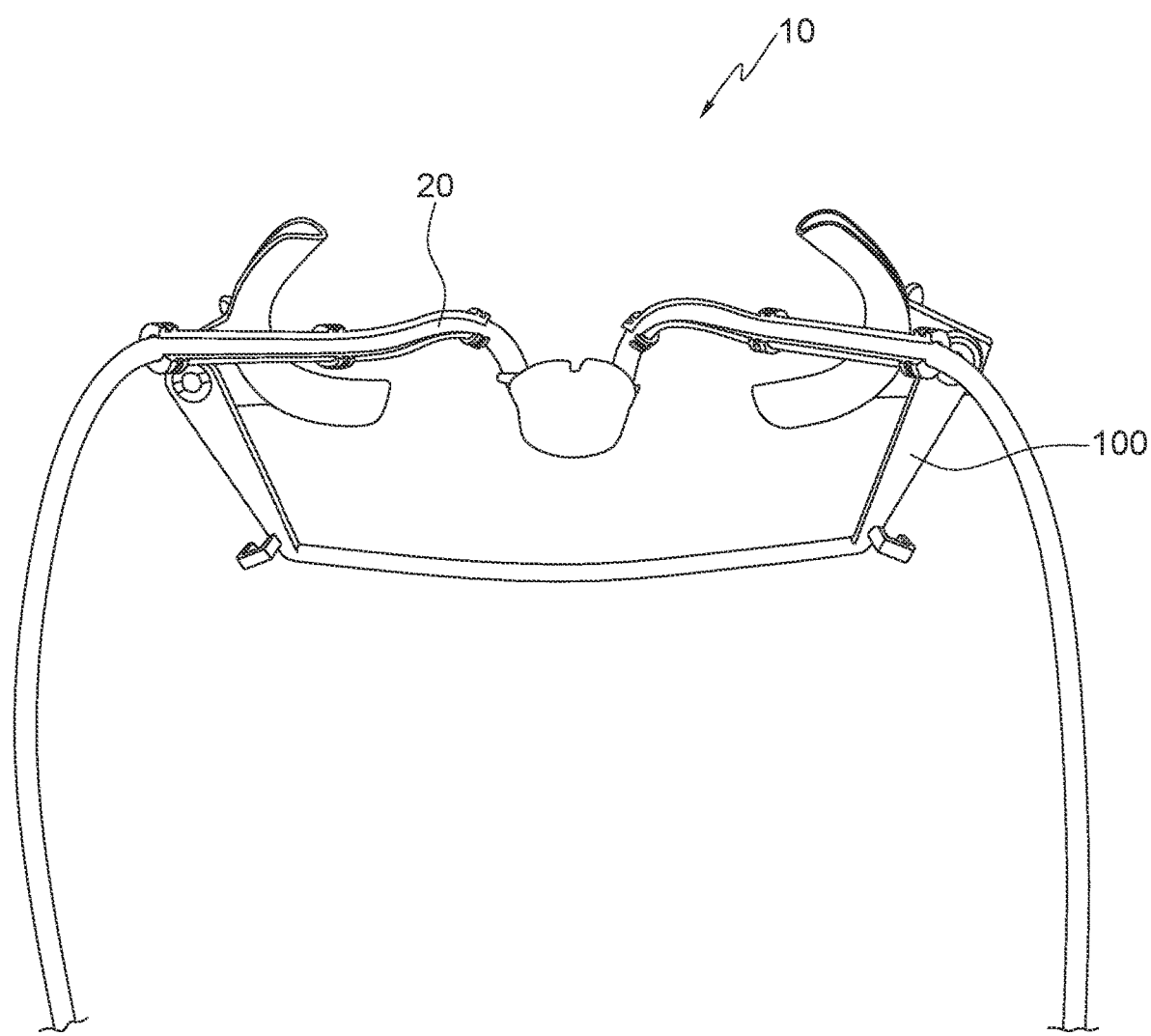
FIG. 1 is a front view of an intra-oral appliance.
Figure 2:
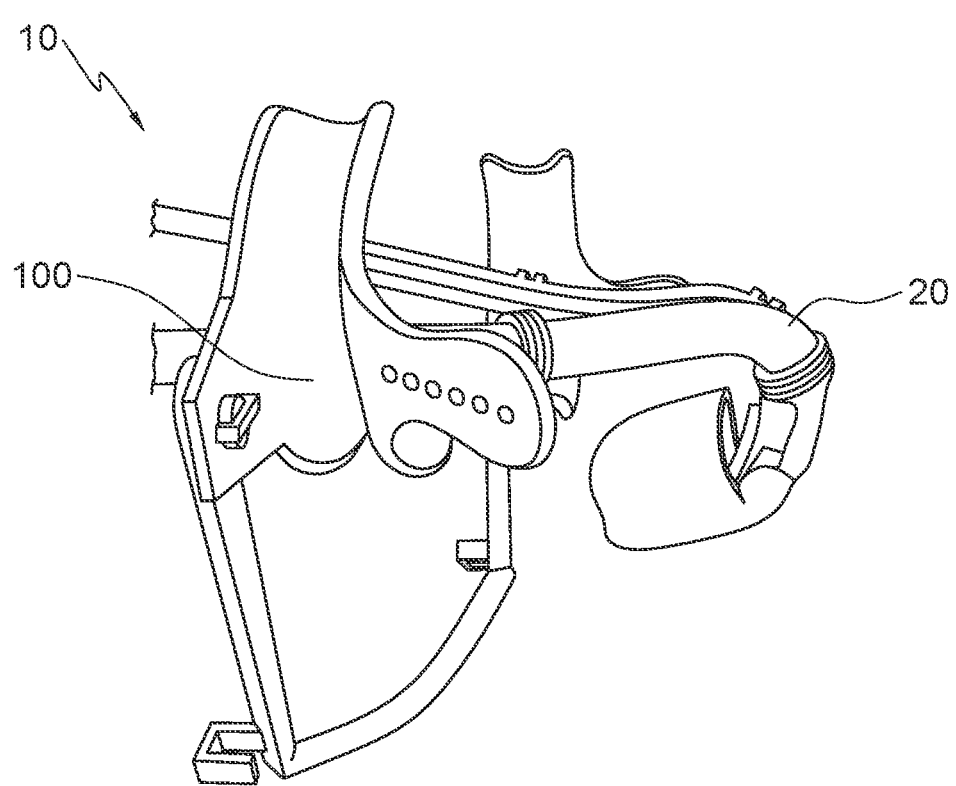
FIG. 2 is side view of the intra-oral appliance of FIG. 1.

Referring to FIGS. 1 and 2, an intra-oral appliance 10 is shown having an internal member 20 and an external member 100 for intra-oral isolation, the separation of a patient's teeth/dental arches from their tongue and mucosa in their mouth, during dental procedures on the patient. The internal member 20 is used for isolation; to isolate the tongue and mucosa in the mouth from the patient's teeth. Optionally, the internal member 20 can also be used for fluid/moisture control; to maintain a dry field in the patient's mouth by removing fluid and debris from the patient's mouth. The external member 100 is used to retract the lips of the patient and hold the patient's mouth open.

Referring to FIGS. 3-6, the internal member 20 can include: a tongue crib 30; a first arm 50; a second arm 55; and; in some aspects, tubing 60.

The tongue crib 30 is used to hold a patient's tongue in order to retract the tongue and isolate it from the dental arches. The tongue crib 30 can have an opening 32 in a back end 34 of the tongue crib 30 and a tongue shaped interior space 40 so that the anterior tip and sides of a patient's tongue are held within the interior space 40 of the tongue crib 30.

Figure 6:
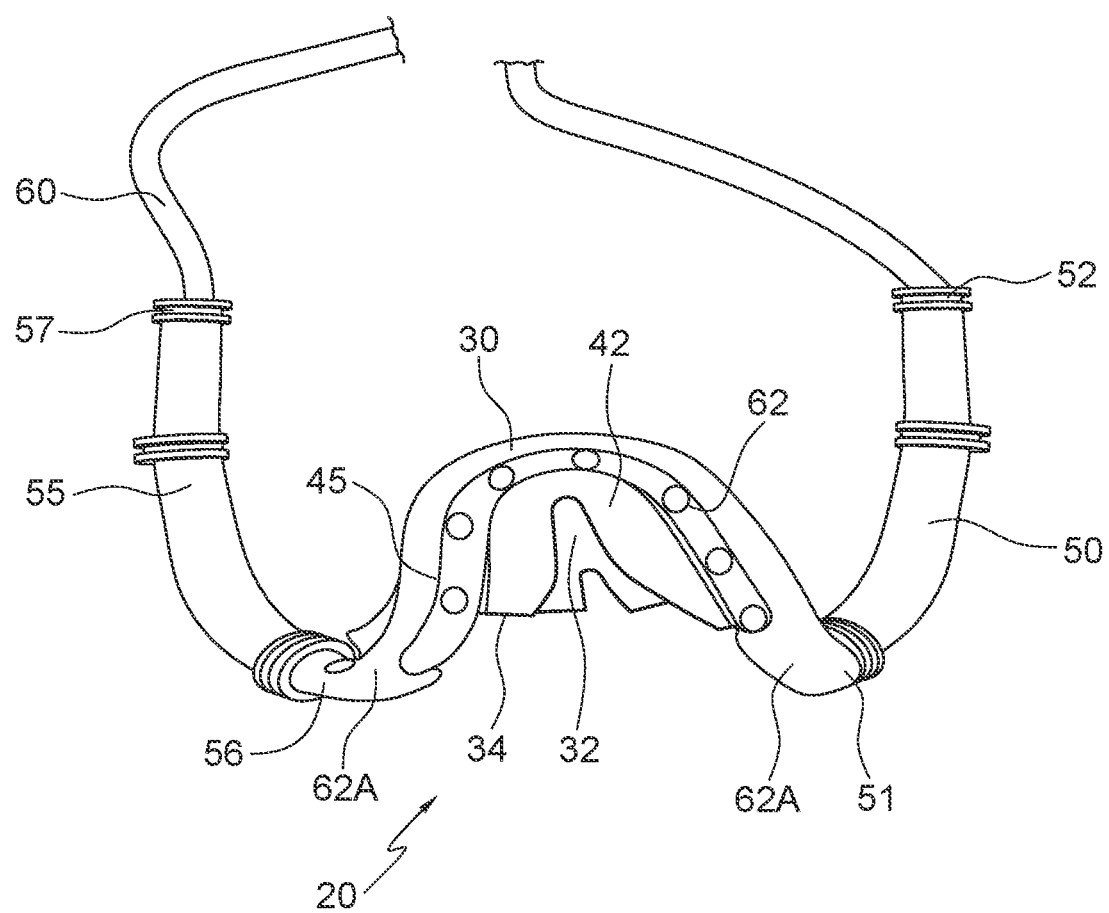
FIG. 6 is a bottom rear view of the internal member of FIG. 3.

Referring to FIG. 6, if tubing 60 is used for fluid control, in addition to just providing isolation, a u-shaped open channel 45 can be provided in a bottom 42 of the tongue crib 30 through which the tubing 60 can be run. The channel 45 can be open on the bottom 42 of the tongue crib 30 to allow the tubing 60 to come in contact with the bottom of the patient's mouth and below their tongue.

Figure 5:
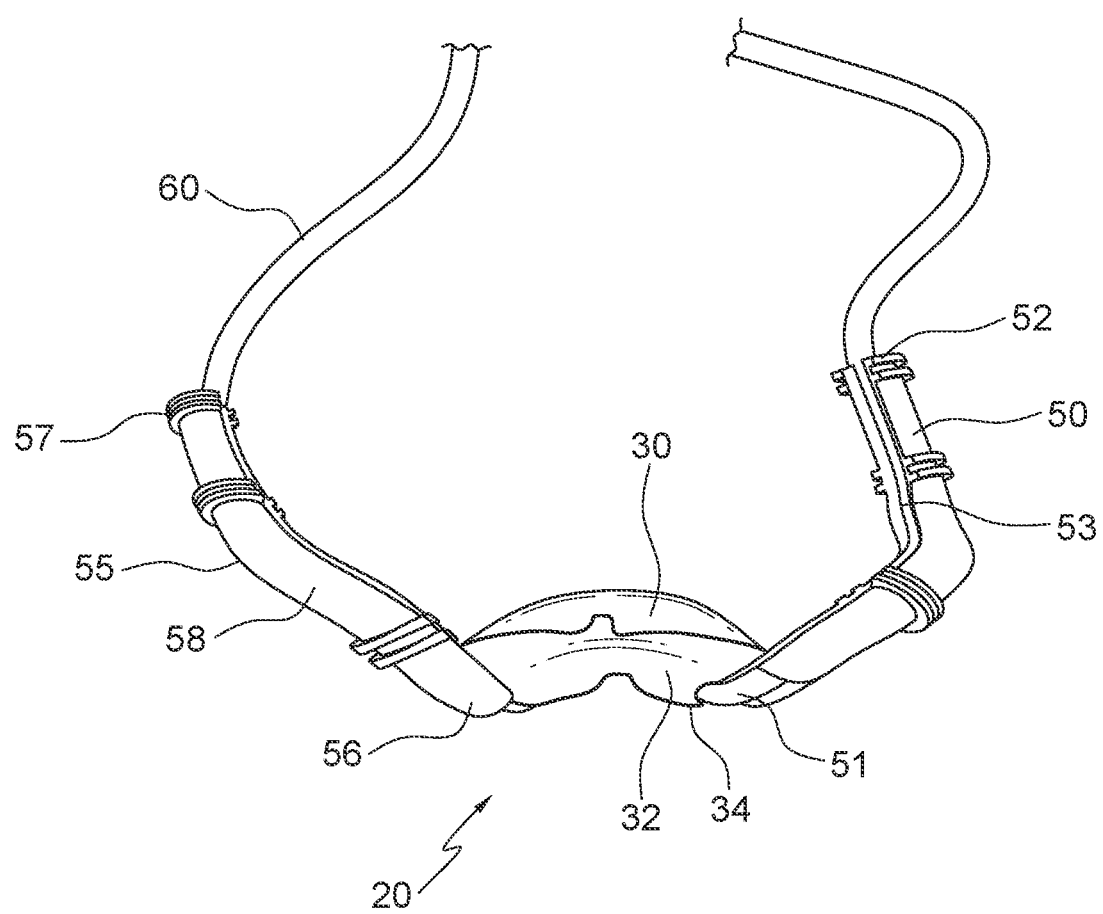
FIG. 5 is a top rear view of the internal member of FIG. 3.

Referring to FIGS. 5-6, the first arm 50 and the second arm 55 can be connected at first ends 51, 55 to the back end 34 of the tongue crib 30. The first arm 50 can extend from the first end 51 to a second end 52 and the second arm 55 can extend from the first end 56 to the second end 57. Both the first arm 50 and the second arm 55 are flexible and poseable so that a user can bend the arms 50, 55 into a desired position and the arms 50, 55 will maintain this position. The first arm 50 and the second arm 55 can undergo intentional plastic deformation and then hold the new shape until moved again. When the tongue crib 30 is inserted into a patient's mouth, the arms 50, 55 will typically be bent into a curve so that the arms 50, 55 extend from the first ends 51, 56 connected to the back end 34 of the tongue crib 30, curve around to extend in an opposite direction from the direction the arms 50, 56 first extend from the back end 34 of the tongue crib 30, continue to curve around until the arms 50, 56 extends towards the patient's mouth and to the second ends 52, 57 of the arms 50, 55, respectively.

The first arm 50 and the second arm 55, because of their poseability, can allow-maximum intercuspation of a patient's teeth, while the internal member 20 is in place, by allowing the first arm 50 and the second arm 55 to be routed behind a patient's molars and pass over his or her retro-molar pad. By being able to position the arms 50, 55 over the patient's retro-molar pad behind the dental arches, the arms 50, 55 will not pass between the patient's upper and lower teeth, allowing the patient to close their upper and lower teeth together (bite) while the internal member 20 is in place and their tongue is positioned in the tongue crib 30. In this manner, the internal member 20 can allow the patient to close their teeth together fully, with the internal member 20 still in place, maintaining isolation and moisture control from the tongue and other intra-oral tissues.

The arms 50, 55, once they are posed over the retro-molar pads, can be bent and posed so that the arms 50, 55 curve and extend between the inside of the patient's cheeks and their teeth towards the patient's lips.

The arms 50, 55 can be long enough so that the aims 50, 55 extend out of the mouth of a patient, past the patient's lips, with the second ends 52, 56 of the arms 50, 55 being positioned outside the mouth of the patient.

If fluid control is desired, in addition to isolation of the teeth and mucosa from the dental arches, the arms 50, 55 can also be provided with channels 53, 58 for running the tubing 60 through the channels 53, 58 to the tongue cradle 30. Channel 53 can run through the first arm 50 and channel 58 can run through second arm 55. The channels 53, 58 can be sized to accept the tubing 60 allowing the tubing 60 to be positioned in these channels 53, 58 so that the tubing 60 runs inside the arms 50, 56.

The channels 53, 58 can correspond the ends of the u-shaped channel 45 in the tongue crib 30. In this manner, the tubing 60 can be inserted in the u-shaped channel 45 in the bottom 42 of the tongue crib 30 and the channels 53, 58 in the first arm 50 and the second arm 50 so that tubing runs through the arms 50, 56 and the tongue crib 30.

Referring to FIG. 6, a series of aperture 62 can be provided passing through the bottom of the tubing 60. When the tubing 60 is provided in the u-shaped channel 45 in the bottom 42 of the tongue crib 30, the apertures 62 in the tubing 60 can be positioned in the portion of the tubing 60 that is inserted in the channel 45 and the tubing oriented so that the apertures 62 are provided in the opening of the channel 45 so that fluid and debris, such as saliva and other foreign substances, in the patient's mouth can come into contact ith these apertures 62.

The apertures 62 can be provided in different locations along the tubing 60 depending on the desired fluid and debris rears val. However, in one aspect, one of the apertures 62, aperture 62A can be provided where the tubing 60 exits the u-shaped channel 45 at the back end 34 of the tongue crib 30 and enters the channels 53, 55 in the arms 50, 55. It is at this location that the tubing 60 can be closest to the bottom of the patient's mouth, likely touching the bottom of the patient's mouth, and therefore most likely to be in contact with fluid pooling in the bottom of the patient's mouth.

Figure 3:
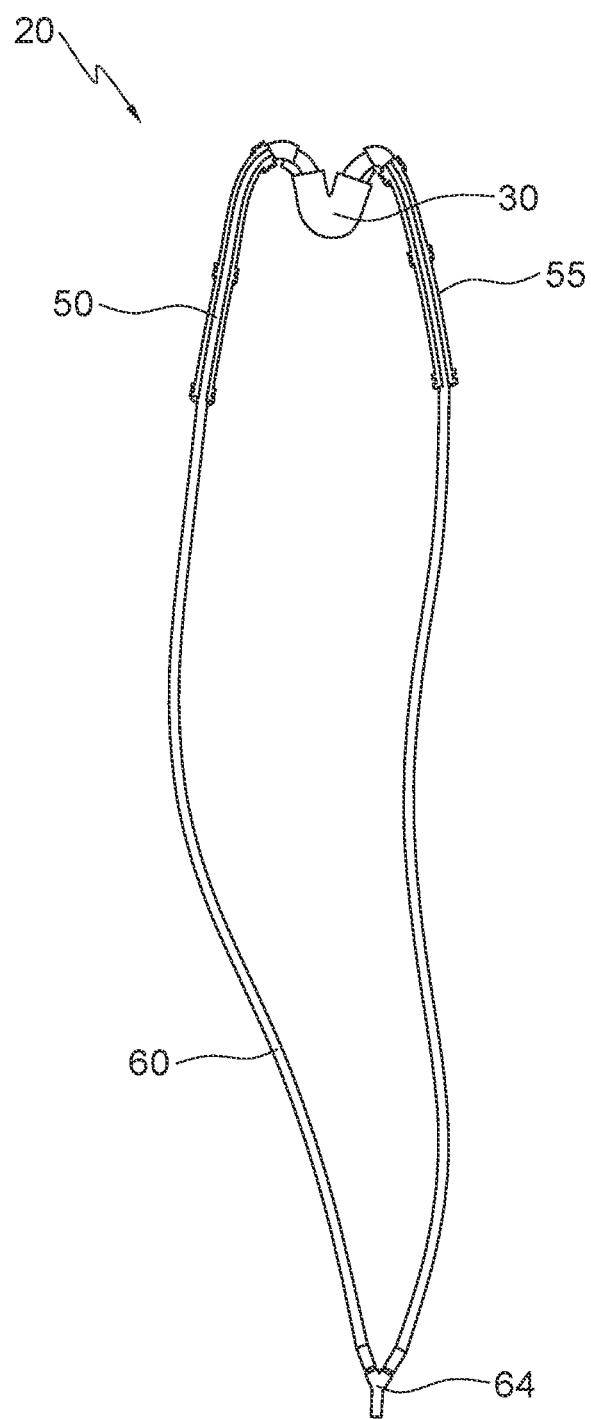
FIG. 3 is a top view of an internal member of an intra-oral appliance.
Figure 4:
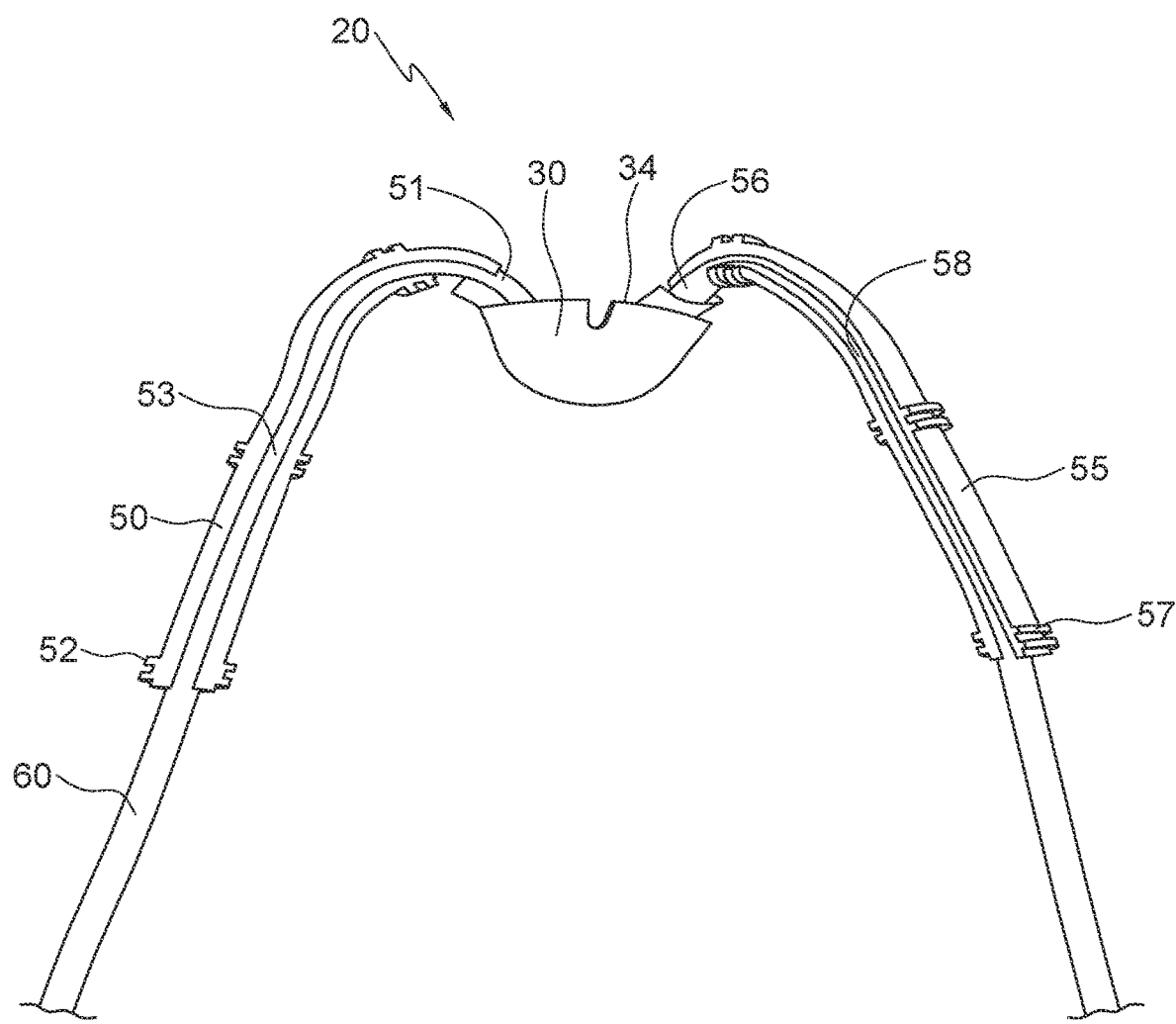
FIG. 4 is a front view of the internal member of FIG. 3.

Referring to FIG. 3, the tubing 60 can be provided with a connector 64 for connecting to a vacuum source to create a vacuum in the tubing.

Figure 13:
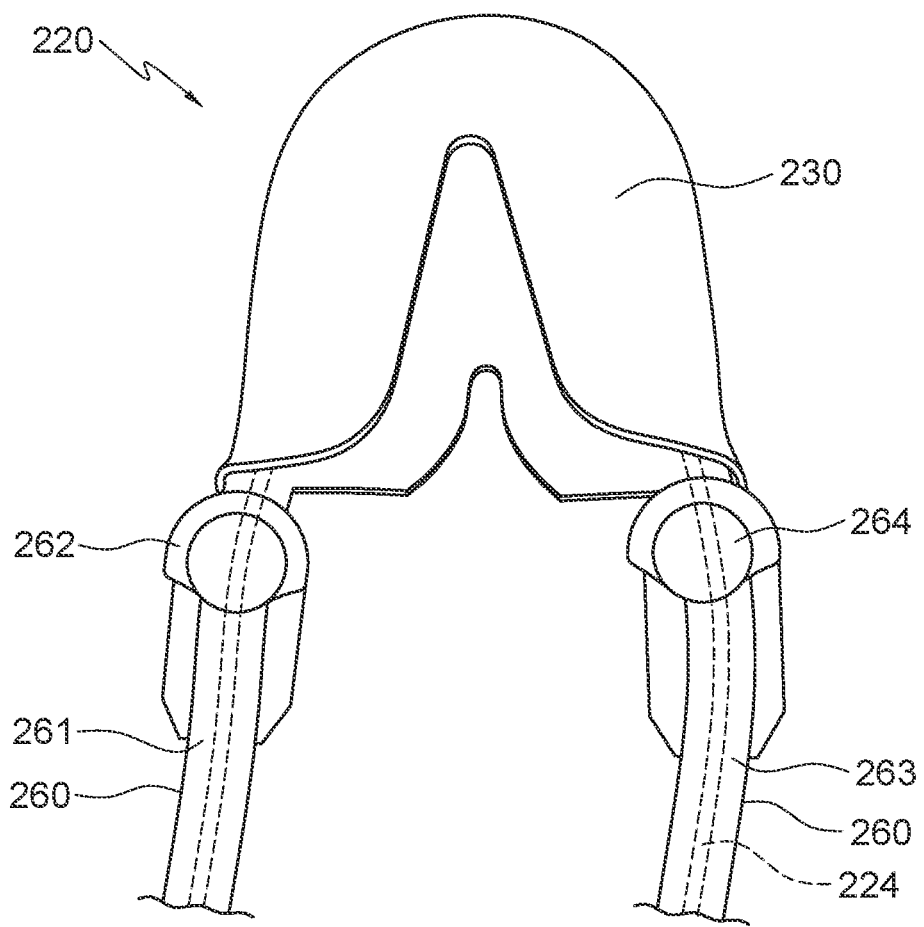
FIG. 13 is a bottom view of an internal member in a further aspect.
Figure 14:
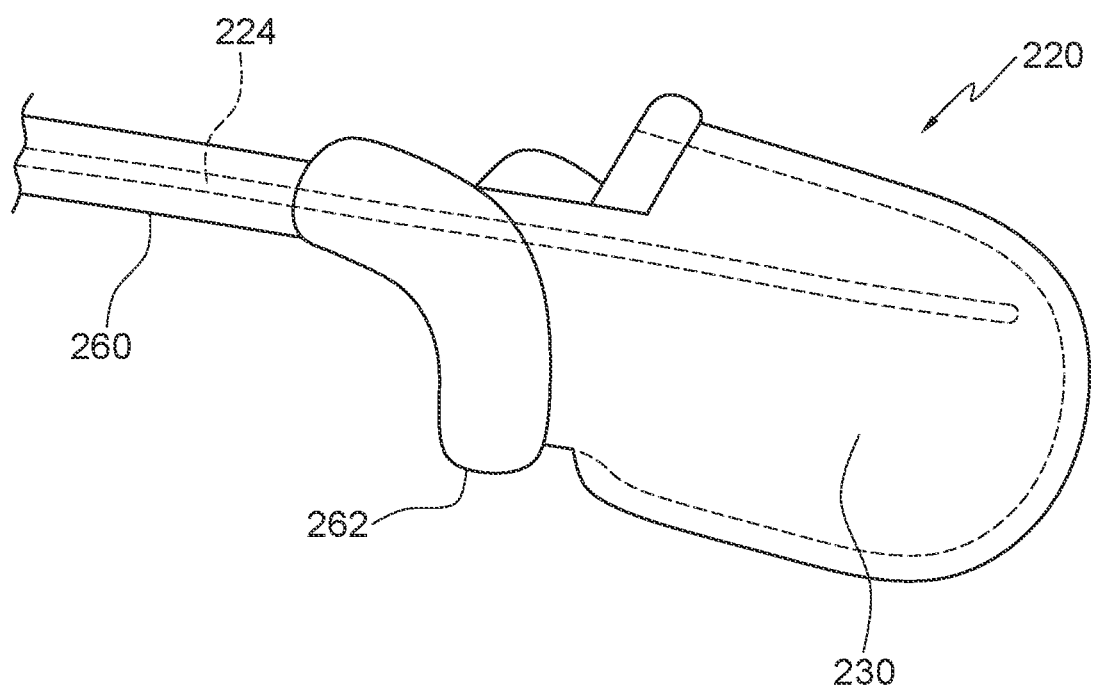
FIG. 14 is a side view of the internal member shown in FIG. 13.
Figure 15:
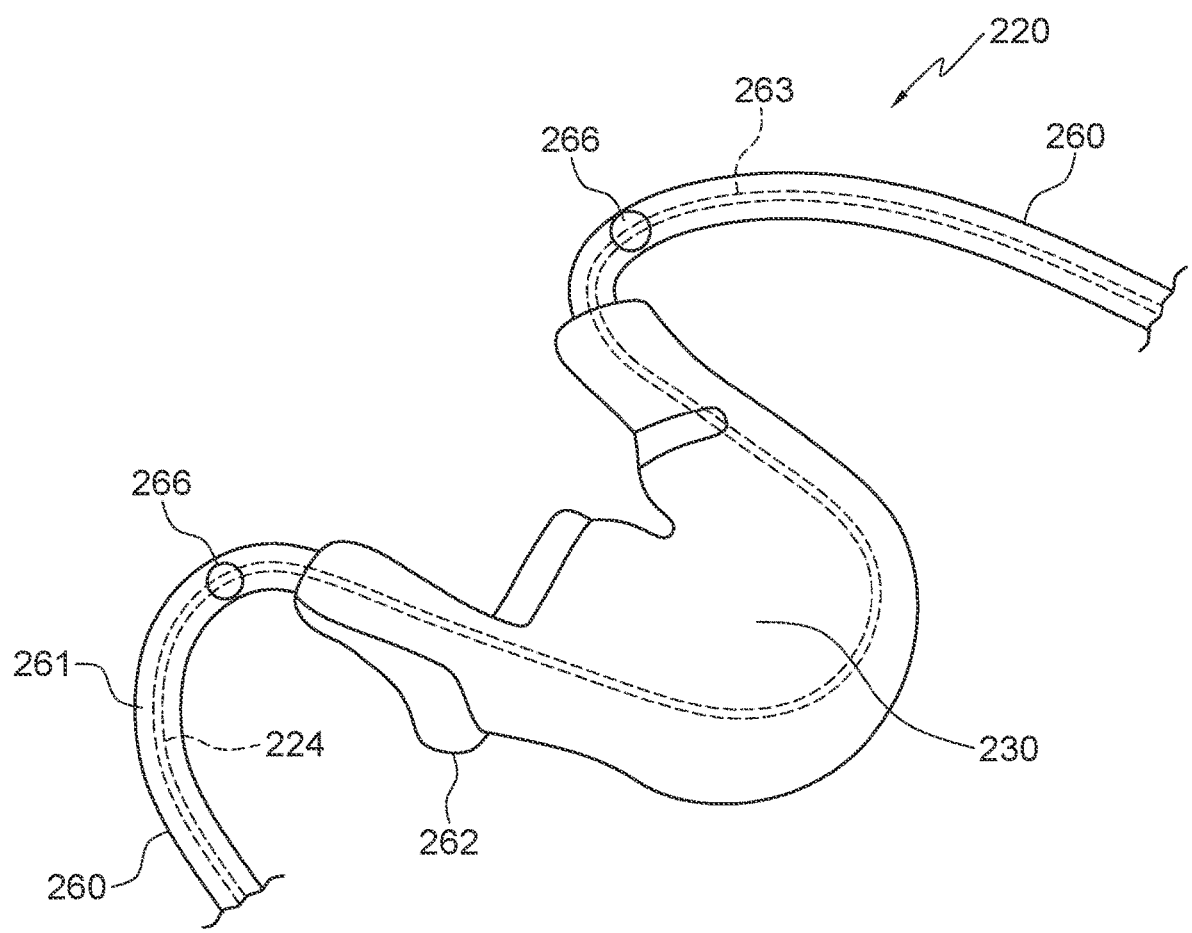
FIG. 15 is a top view of the internal member shown in FIG. 13.

FIGS. 13-15 illustrate an internal member 220 in another aspect. Internal member 220 can be similar to internal member 20, but internal member 220 has a poseable wire 224 integrated with the tubing 260 to form a poseable first arm 261 and a poseable second arm 263. A tongue crib 230 is separated from the tubing 260 and the first and second arms 261, 263.

The poseable wire 224 is positioned to run through or inside the tubing 260 so that the poseable wire 224 can allow the tubing 260 to be poseable as well. However, at the end of the tubing 260 the wire 224 can pass out of the tubing 260 and into the tongue crib 230 which is physically separate from the tubing 260. In this manner, the poseable wire 224 can run through a first side of the tubing forming the poseable first arm 261, out an end of the tubing 260 on a first side of the internal member 220 and run into the tongue crib 230. The wire 224 can bridge the physical gap between the end of the tubing 260 and the tongue crib 230. In the tongue crib 230, the poseable wire 224 can run around a bottom periphery of and inside the tongue crib 230, before the wire 224 exits the tongue crib 240 and runs into an end of the tubing 260 on the second side of the tubing forming the poseable second arm 263 of the internal member 220.

The poseable wire 224 allows the tubing 260 to act as poseable arms with the poseable first arm 261 and the poseable second arm 263. This allows the tongue crib 230 to be moveable on the poseable first arm 261 and second arm 263 so that the user can position the tongue crib 230 in a desired place in the patient's mouth and the poseable wire 224 running through the tubing 260 can cause the tongue crib 230 to remain in the position it is moved to.

The internal member 220 can also be provided with apertures to allow fluid control in the patient's mouth. A first sub-lingual apertures 262 can be provided at the end of the first arm 261 of the internal member 220 and a second sub-lingual aperture 264 can be provided at the end of the second arm 264 of the internal member 220. These sub-lingual apertures 262, 263, in one aspect, can be the open ends of the tubing 260, at the ends of the first arm 261 and the second aim 263, oriented to face downwards in the patient's mouth when the internal member 220 is placed in the patient's mouth to collect fluids and other materials from under the patient's tongue.

Retromolar pad apertures 264 can be provided passing out of the tubing 260 positioned in the first arm 261 and the second arm 263 where the tubing 260 will pass over the patient's retromolar pad when the internal member 220 is positioned in place in the patient's mouth. When a patient is lying back in the chair, saliva and other fluids in the patient's mouth will to run downwards, towards the back of the patient's mouth and collect at the patient's retromolar pad where this fluid can be evacuated through the retromolar pad apertures 264 and into the tubing 260 to be removed by the internal member 220.

In a further aspect, a hygienist's design can have no sub-lingual apertures and the wire gauge of the poseable wire 224 can be chosen to provide less resistance to tongue movement allowing the patient to pose the tongue crib in a desired location 230.

In some aspects, the internal member 20 can be used alone to isolate a patient's dental arches from his or her tongue and mucosa, with the arms 50, 55 being posable, but requiring enough force to deform, so that the arms 50, 55 can also brace the patient's lips open by bending the arms 50, 45 outward against the patient's lips. However, referring again to FIGS. 1 and 2, the external member 100 can be used to keep a patient's mouth open when the intra-oral appliance 10 is in use by spreading the lips of the patient and also to hold the internal member 20 in position relative to the external member 100.

Figure 7:
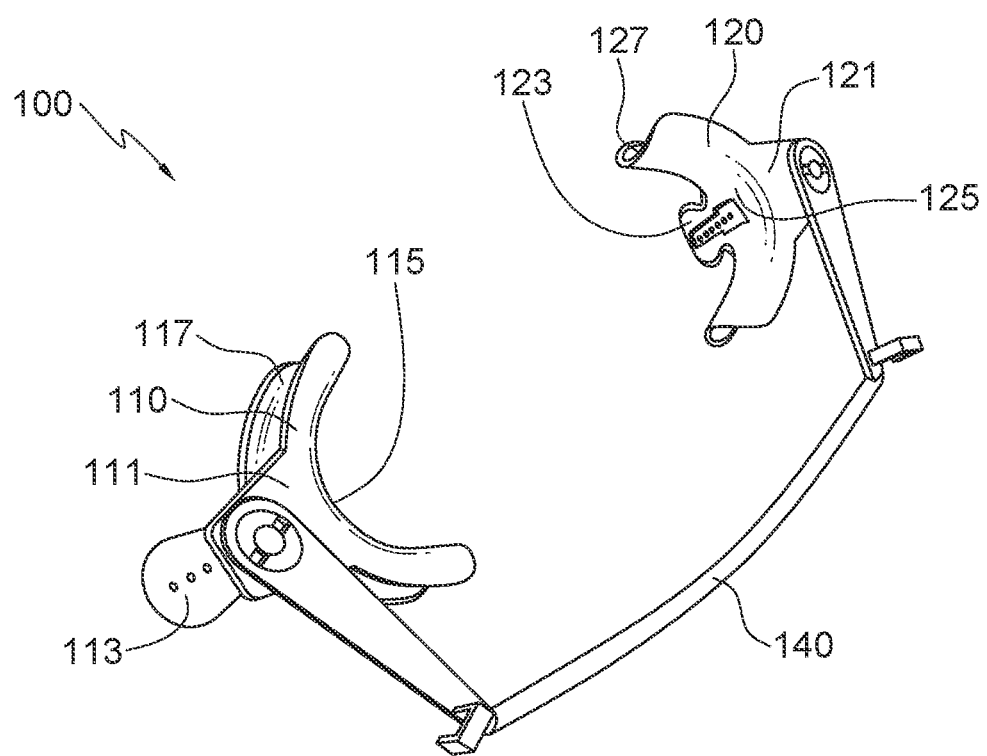
FIG. 7 is a perspective view of an external member of an intra-oral appliance.
Figure 8:
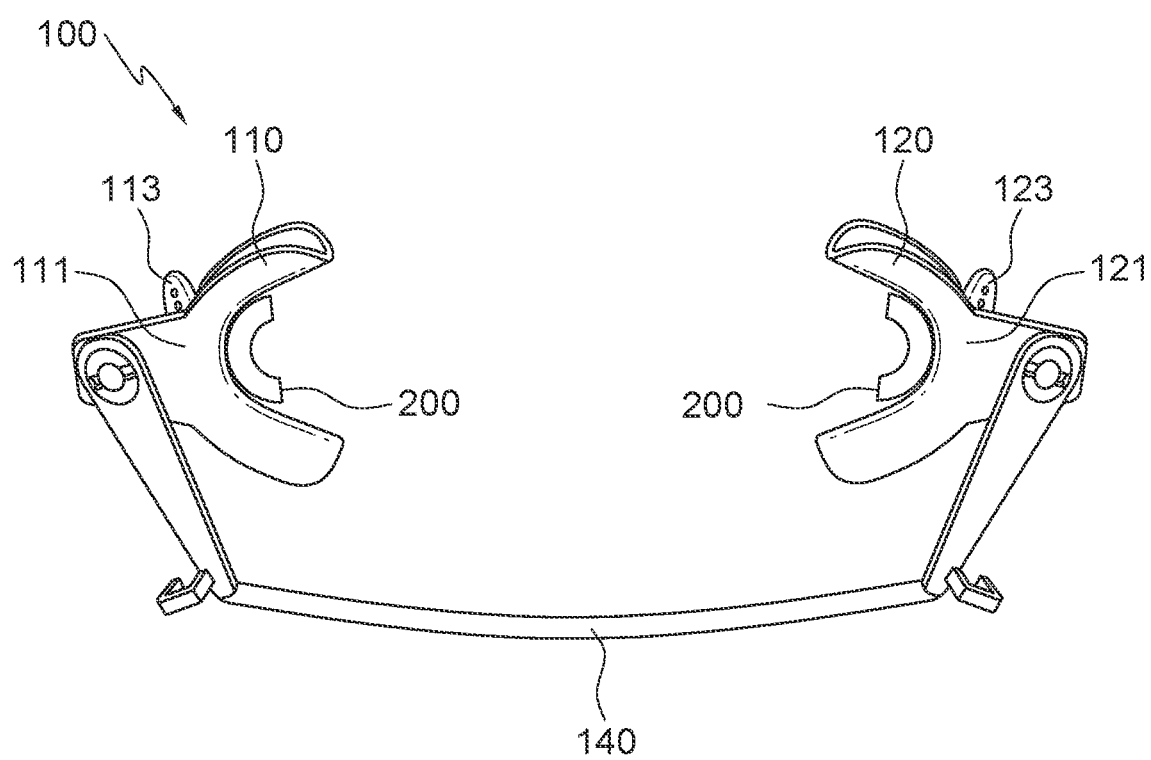
FIG. 8 is a front view of the external member of FIG. 7.
Figure 9:
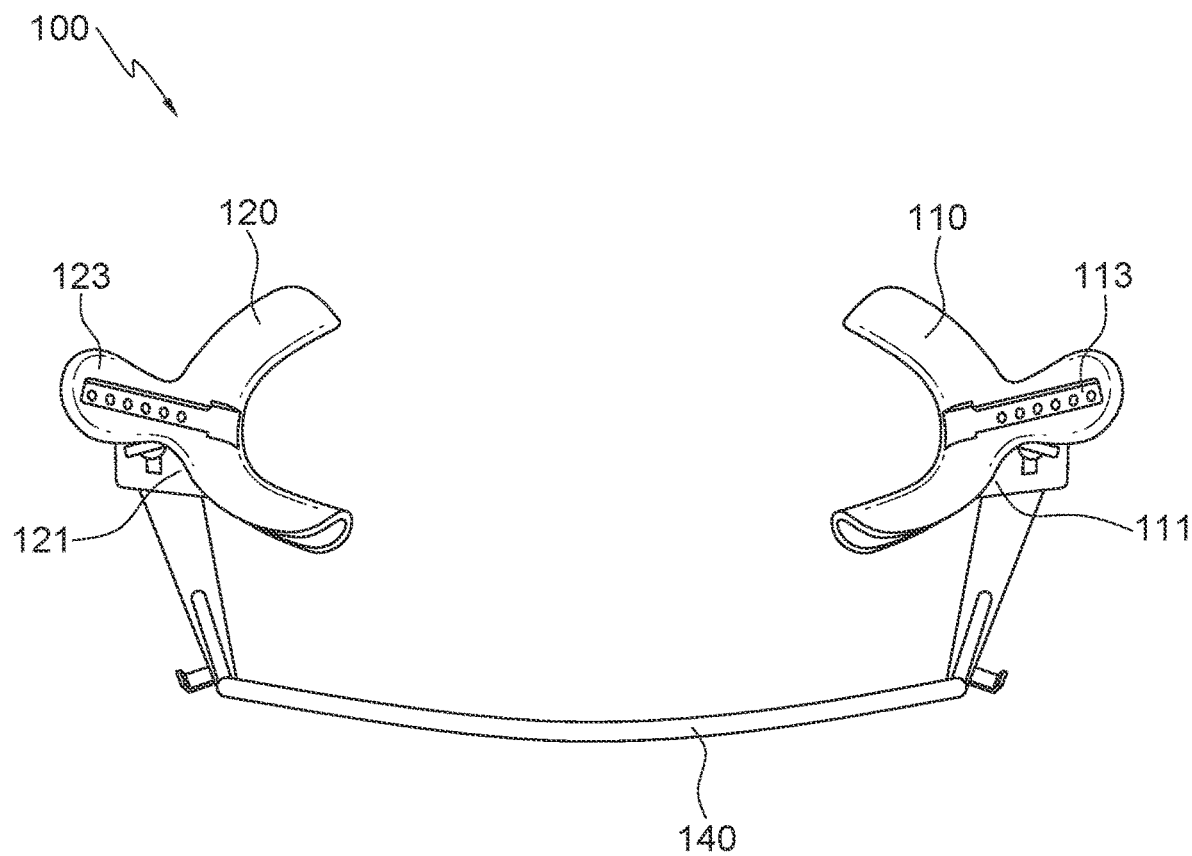
FIG. 9 is a rear view of the external member of FIG. 8.
Figure 10:
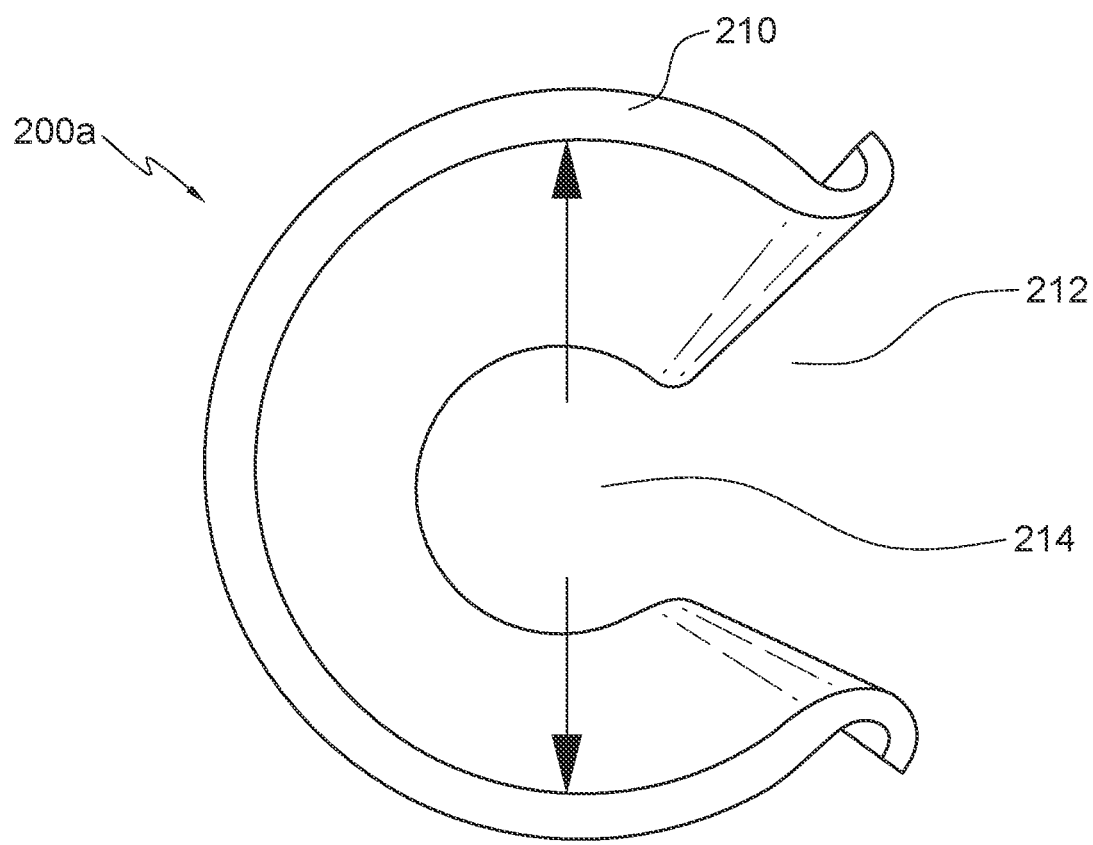
FIG. 10 is a front view of a connector in one aspect.

Referring to FIGS. 7-9, the external member 100 can include a first lip retractor 110, a second lip retractor 120, a first retractor flange 111, a second retractor flange 121, a first wing member 113, a second wing member 123, a flexible resilient member 140 and connectors 200.

The first and second lip retractors 110, 120 are used to hold the patient's lips open. The first and second lip retractors 110, 120 can each have a generally, arcuate shape with a inner surface 115, 125, respectively, and an outer surface 117, 127, respectively. The outer surfaces 117, 127 can have an open channel with a substantially semi-circular cross-section so that a patient's lips will come into contact with this outer surface 117, 127 and the lips will be held in place on the lip retractors 110, 120 within the semi-circular channels.

The first retractor flange 111 can be connected to the first lip retractor 110 at a front end of the first lip retractor 110 and extending outwards from the outer surface 117, 127 of the first lip retractor 110. The second retractor flange 121 can be connected to the second lip retractor 120 at a front end of the second lip retractor 120 and extending outwards from the outer surface 117, 127 of the second lip retractor 120.

The first wing member 113 can be attached to the first lip retractor 110 extending backwards into the mouth of the patient and angled outwards when the external member 100 is positioned holding open a patient's lips. The inner surface of the first wing member 113 can align with the inner surface 115 of the first lip retractor 110 where the first wing member 113 connects with the first lip retractor 110.

The second wing member 123 can be attached to the second lip retractor 120 extending backwards into the mouth of the patient and angled outwards when the external member 100 is positioned holding open a patient's mouth. The inner surface of the second wing member 123 can align with the inner surface 125 of the second lip retractor 120 where the second wing member 123 connects with the second lip retractor 120.

The flexible resilient member 140 can be connected between the first retractor flange 111 and the second retractor flange 121 and can act as a biasing member to spread the first retractor flange 111 and the second retractor flange 121 apart and therefore the first lip retractor 110 and the second lip retractor 120 apart from one another.

The connectors 200, shown in FIG. 8, can be attached to the inner surface 115, 125 of the lip retractors 110 to hold the arms 50, 55 of the internal member 10 and therefore hold the internal member 10 in a position relative to the external member 100. In one aspect, the connectors 200 allow quick and easy attachment to the arms 50, 55 of the internal member 10.

Referring to 10, shows a connector 200a, in one aspect, that comprises an elongate c-shaped member 210 defining an opening 212 and an interior space 214. An arm 50, 55 of the internal member 20 can be inserted through the opening 212 in the c-shaped member 210 and into the interior space 214 where the arm 50, 55 will be held in place in the connector 200a. The connector 200a can be attached to the inner surface 115, 125 of the lip retractors 110.

Figure 11:
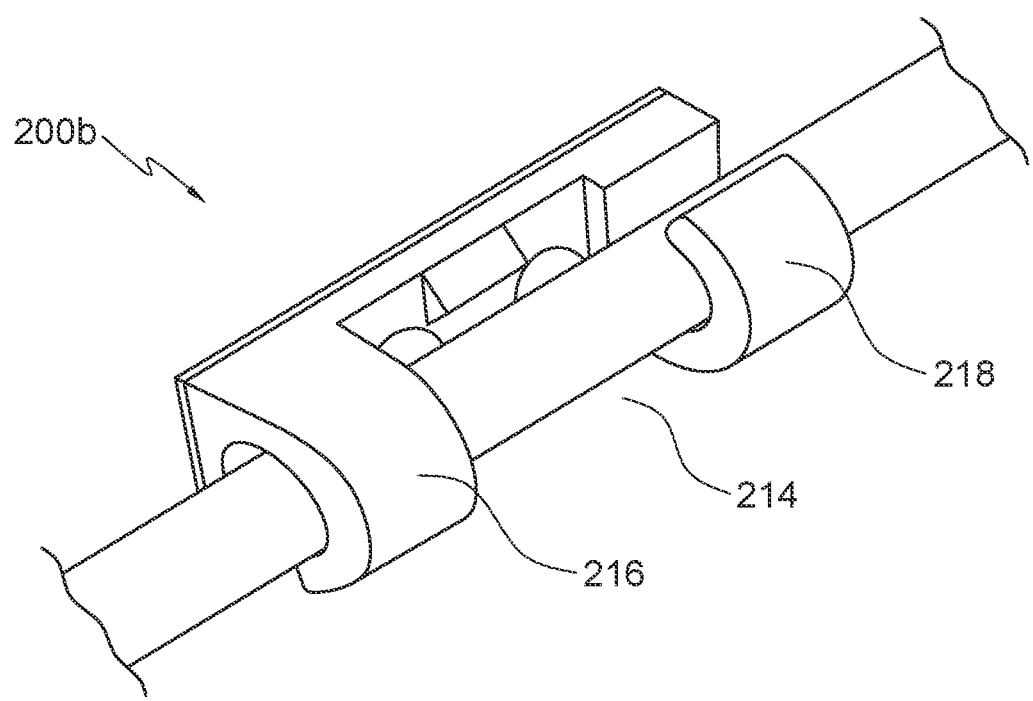
FIG. 11 is a perspective view of a connector in another aspect.

Referring to FIG. 11, a connector 200b, in another aspect is shown, where two dips, one downward facing clip 216 and one upwards facing clip 218, are used to hold an arm 50, 55 of the internal member 20 in place. The downward facing clip 216 and the upward facing clip 218 are separated by a horizontal spacing 224. The connector 200b can be attached to the inner surface 115, 125 of the lip retractors 110.

Figure 12:
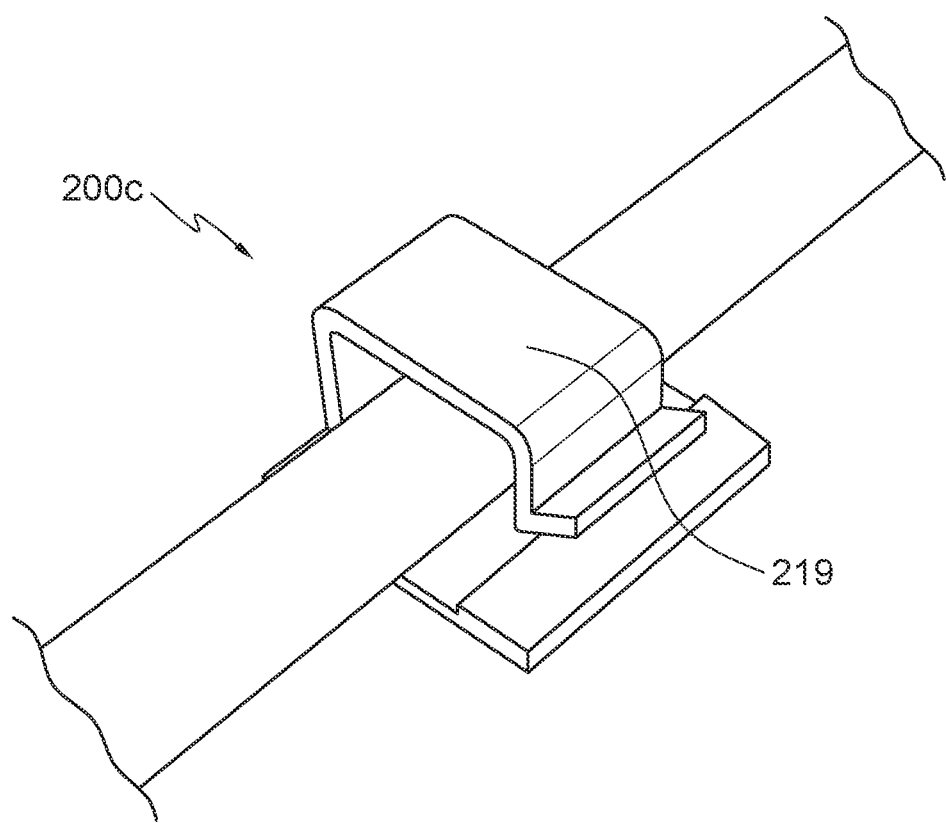
FIG. 12 is perspective view of a connector in another aspect.

Referring to FIG. 12, a connector 200c, in another aspect is shown, where a clip 219 is used to hold an arm 50, 55 of the internal member 20 in place. The connector 200c can be attached to the inner surface 115, 125 of the lip retractors 110.

In operation, the intra-oral appliance 10 can be inserted into a patient's mouth for intra-oral isolation; to separate the patient's teeth from their tongue and mucosa in their mouth, during dental procedures on the patient. Additionally, the intra-oral appliance 10 can be used, once it is positioned in the patient's mouth to create a dry field in their mouth by removing fluid and other materials from the patient's mouth.

Figure 16:
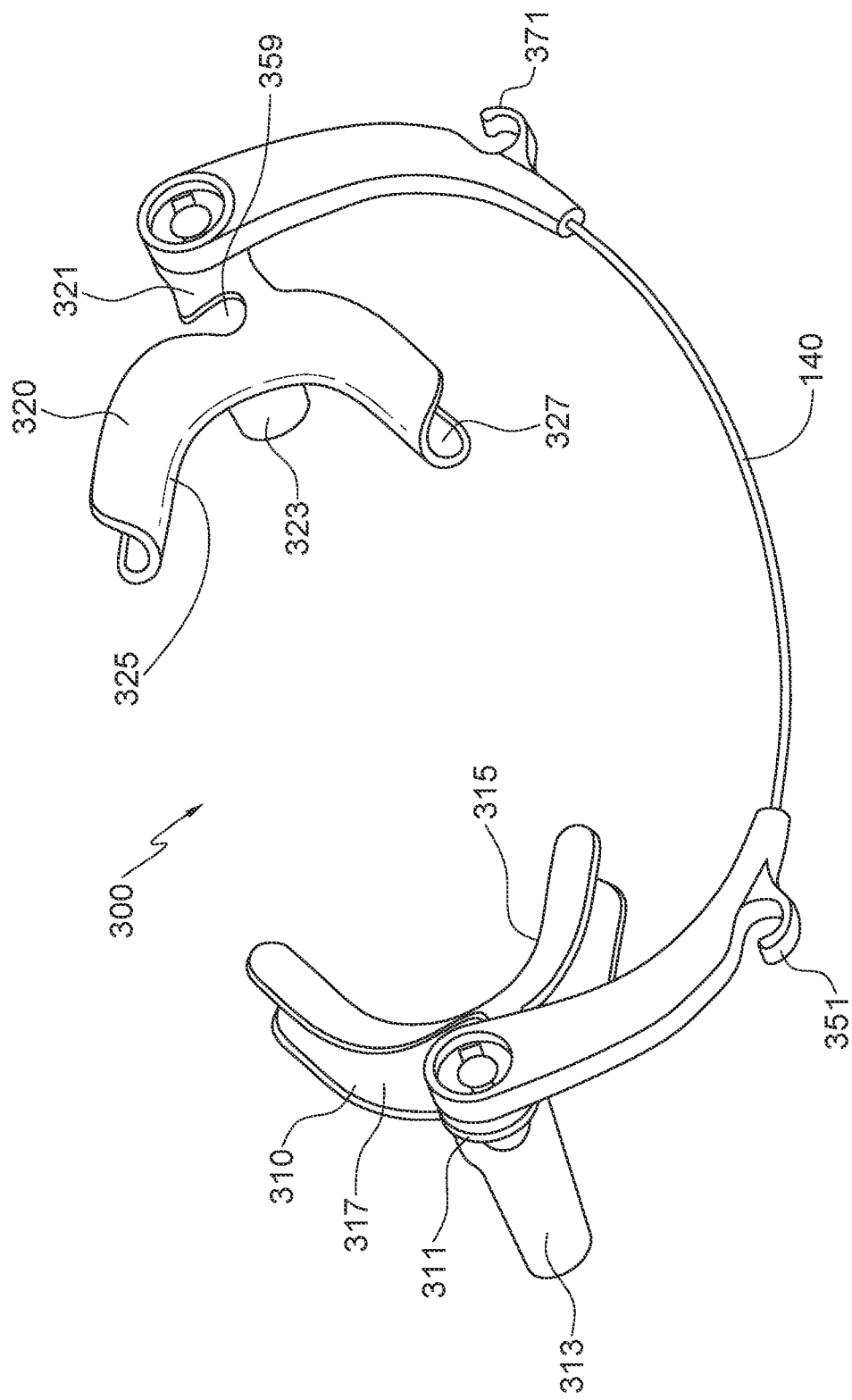
FIG. 16 is perspective view of an external member in a further aspect.
Figure 17:
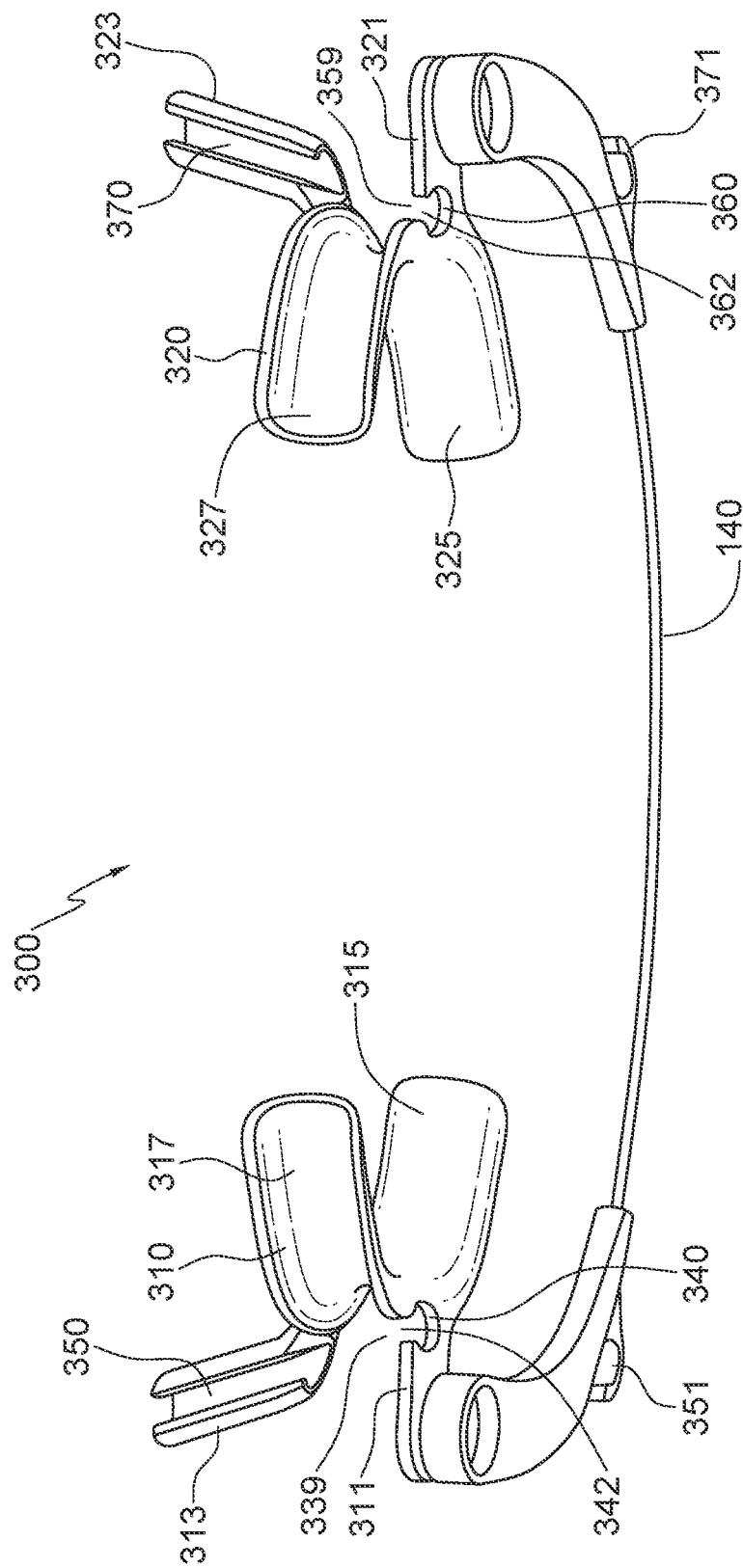
FIG. 17 is a top perspective view of the external member shown in FIG. 16.

Referring to FIGS. 16 and 17, a further external member 300 is shown. The external member 300 can include a first lip retractor 310, a second lip retractor 320, a first retractor flange 311, a second retractor flange 321, a first wing member 313, a second wing member 323, a flexible resilient member 140, a first connector 339, a second connector 359, a first clip 351 and a second clip 371.

Like the first and second lip retractor 110, 120 on the external member 100, the first lip retractor 310 and second lip retractor 320 can be used to hold the patient's lips open and each can have a generally, arcuate shape with an inner surface 315, 325 and an outer surface 317, 327. The outer surfaces 317, 237 can have an open channel with a substantially semi-circular cross-section so that a patient's lips will come into contact with these outer surfaces 317, 327 and their lips will be held in place on the lip retractors 310, 320 within the semi-circular channels. However, the lip retractors 310, 320 can have provisions for tubing or arms of an internal member to be connected behind the outer surfaces 317, 327 so that the connected tubing or arms will pass into a patient's mouth between the patient's oral commissure and the outer surfaces 317, 327 of the lip retractors 310, 320.

The lip retractor 310 can have a first retractor flange 311 and be connected to the lip retractor 310 at a front end of the lip retractor 310 and extending outwards from the outer surface 317 of the lip retractor 310. The lip retractor 320 can have a retractor flange 321 that is connected to the lip retractor 320 at a front end of the lip retractor 320 and extending outwards from the outer surface 327 of the lip retractor 320.

A first wing member 313 can be attached to the lip retractor 310 extending backwards into the mouth of the patient and angled outwards when the lip retractor 310 is positioned holding open a patient's lips. The inner surface of the first wing member 313 can align with the inner surface 315 of the lip retractor 310 where the wing member 313 connects with the lip retractor 310. A second wing member 323 can be attached to the lip retractor 320 extending backwards into the mouth of the patient and angled outwards when the lip retractor 320 is positioned holding open a patient's lips. The inner surface of the first wing member 323 can align with the inner surface 325 of the lip retractor 320 where the wing member 323 connects with the lip retractor 320.

A flexible resilient member 140 can be connected between the retractor flange 311 on the first lip retractor 310 and the retractor flange 321 on the second lip retractor 320. The flexible resilient member 140 can act as a biasing member to spread the first retractor flange 311 and the second retractor flange 321 on the other side of the external member 300 apart and therefore the lip retractor 310 and the lip retractor 320 apart from one another.

Tubing, if internal member 20 is used, or arms 261, 263, if internal member 220 is used, can be connected to the lip retractors 310, 320 through first and second connectors 339, 371 having apertures 340, 360 passing through the retractor flanges 311, 321, respectively. A channel 350 can be provided in the retractor wing 313 and a channel 370 can be provided in the retractor wing 313. In one aspect, each aperture 340, 360 can have an opening 342, 361 on an edge at a top of the retractor flange 311, 321, respectively. This allows a user to use the connectors 339, 359 to connect an internal member, such as internal member 20 or internal member 220, to insert tubing or an arm through the opening 342 in the edge of the retractor flange 311 and into the aperture 340 and tubing or an arm through the opening 362 in the edge of the retractor flange 321 and into the aperture 360. This can allow the tubing of the internal member 20 or the arms 261 of the internal member 220 that is already inserted in the patient's mouth to be inserted through the openings 342, 362 into the apertures 340, 360 to be held in place in the lip retractors 310, 320 without having to remove the internal member 20 or internal member 220 from the patient's mouth.

The channels 350, 370 can be generally c-shaped and sized to allow tubing or arms 261, 263 to be inserted in the channels 350, 370. The channels 350, 370 can each have a length so that a length of the tubing or length of one of the arms 261, 263 can be supported in the channels 350, 370.

To secure tubing running into the patient's mouth for moisture control and to create a dry bed when the external member 300 is being used, the tubing can be inserted into the apertures 340, 360 passing through the retractor flanged 311, 321, respectively. The tubing can then he inserted into the channels 350, 370 provided on the retractor wings 313, 323. When the external member 300 is position in a patient's mouth, the lip retractors 310, 320 are positioned to hold the patient's lips open and the tubing, secured in the aperture 340 and the channel 350 on the first lip retractor 310, will pass through the opening formed between the patient's oral commissure and the outer surface 317 of the lip retractor 310. The tubing secured in the aperture 360 and the channel 370 on the second lip retractor 320, will pass through the opening formed between the patient's oral commissure and the outer surface 327 of the lip retractor 320. In this manner, the tubing will not run in between the inner surface 315 of the lip retractor 310 and the inner surface 325 of the lip retractor 320, freeing up space for the dentist, hygienist, etc. to work in the patient's mouth.

The clips 351, 371 can be used to route tubing around the patient, by holding the tubing extending out of the patient's mouth through the apertures 340, 360.

To secure arms 261, 271 of the internal member relative to the external member 300, the arms 261, 271 can be inserted into the apertures 340, 360 passing through the retractor flanged 311, 321, respectively. The arms 261, 271 can then be inserted into the channels 350, 370 provided on the retractor wings 313, 323. When the external member 300 is position in a patient's mouth, the lip retractors 310, 320 are positioned to hold the patient's lips open and the first arm 261, of the internal member 220, secured in the aperture 340 and the channel 350 on the first lip retractor 310, will pass through the opening formed between the patient's oral commissure and the outer surface 317 of the lip retractor 310. The second ami 271 secured in the aperture 360 and the channel 370 on the second lip retractor 320, will pass through the opening formed between the patient's oral commissure and the outer surface 327 of the lip retractor 320. In this manner, the arms 261, 271 will not run in between the inner surface 315 of the lip retractor 310 and the inner surface 325 of the lip retractor 320, freeing up space for the dentist, hygienist, etc. to work in the patient's mouth.

Referring to FIGS. 1-9, the external member 100 can be used to hold open a patient's mouth. The user can squeeze the first lip retractor 110 and the second lip retractor 120 towards one another, overcoming the biasing forced provided by the flexible resilient member 140 biasing the first lip retractor 110 and the second lip retractor 120 outwards, so that the lip retractors 110, 120 and the wing member 113, 123 can be inserted into the patient's mouth with the wing member 113, 123 and the rear ends of the lip retractors 110, 120 inside the patient's mouth until the channels in the outer surfaces 117, 127 of the lip retractors 110, 120 line up with the lips of the patient. The retractor flanges 111, 121 and the flexible, resilient member 140 will remain outside the patient's mouth and in front of their cheeks and chin.

The user can then slowly stop squeezing the lip retractors 110, 120 towards one another, allowing the biasing force of the resilient member 140 to once against spread apart the first lip retractor 110 and the second lip retractor 120 until the outer surfaces 117, 127 of the lip retractors 110, 120 come in contact with the patient's lips and then lightly force the patient's lips outwards.

With the external member 100 positioned holding open the mouth of the patient, the internal member 20 can be inserted into the mouth of the patient. The tongue cradle 30 can be inserted first through the lips of the patient that are now being held open by the external member 100. The tongue cradle 30 can be inserted with the opening 32 in the back end 34 of the tongue crib 30 being inserted first. The internal member 20 can be maneuvered so the patient's tongue is inserted through the opening 32 until the anterior tip and sides of the tongue are positioned in the interior space 40 of the tongue crib 30.

With the patient's tongue in the tongue cradle, the arms 50, 55 can be posed so that they run behind the patient's dental arches and over the retro-molar pad. The arms 50, 55 can then be bent to curve forwards and extend frontwards, running between the dental arches and the patient's inner cheeks, before extending out the open mouth of the patient. The arms 50, 55 of the internal member 20, which extend out of the patient's mouth, can be connected by the connectors 200 to the external member 100 to secure the internal member 20 in position relative to the external member 100 and if tubing 60 is used in the internal member 20, the tubing 60 can be connected to a vacuum source (not shown).

Alternatively, the internal member 20 can be connected to the external member 100 before the external member 20 is positioned in the patient's mouth and the tongue crib 30 inserted into the patient's mouth before the wing member 113, 123 and lip retractors 110, 120 of the e e member 20 are inserted into the patient's mouth.

In use, the user can move the tongue crib 30 to various positions to move the patient's tongue out of the way. The flexible, posable arms 50, 55 allows the user to position and re-position the tongue crib 30 attached to the arms 50, 55 as needed for the user to gain access to different teeth, by simply moving the tongue crib 30 to the new desired position. The poseable arms 50, 55 can then hold the tongue crib 30 in the new position.

Because the poseable arms 50, 55 can be positioned to run behind the dental arches and over the retro-molar pad, the patient can still close their upper teeth against their lower teeth without the internal member 20 interfering with the patient's bite. This is especially beneficial with certain types of dental procedures, such as tooth restorations, because it allows the intra-oral appliance 10 to be kept in place in the patient's mouth, but still allow the patient's teeth to be closed, without having to remove the intra-oral appliance 10. This allows the patient's bite to be checked to see if it is correct before removing the intra-oral appliance 10.

The connector 200 can allow the user to quickly adjust the length of the portion of the arms 50, 55 that are extending into the patient's mouth. The user can remove one or both of the arms 50, 55 of the connectors 200 to reduce the length of the portion of the arms 50, 55 extending into the patient's mouth or extend the length as desired or needed.

If the intra-oral appliance 10 is to be used for fluid control in addition to isolation, to create a dry field in the patient's mouth, the tubing 60 can be connected to a vacuum source 60 to create suction in the tubing 60. Fluid and other debris can be suctioned through the apertures 62 and into the tubing 60 to be carried through the tubing 60 to create a dry field in the patient's mouth.

Once the intra-oral appliance 10 is done being used and removed from the patient's mouth, the internal member 20 and the external member 100 can be separated. The internal member 20 can be disposed of, such as if it cannot be safely or sufficiently sterilized, depending on the material making up the internal member 20 and whether or not tubing 60 is used. In one aspect, the internal member 20 would be made of silicon molded over poseable wire, which can be hard to sterilize. The external member 100 can be made of a more rigid plastic so it may lend itself to sterilization more readily than the internal member 20. In this manner, by having the intra-oral 10 made up of two pieces, the internal member 20 and the external member 100, the internal member 20 can be disposed of after each use and the external member 100 sterilized and reused with a new internal member 20 for each new patient.

Figure 18:
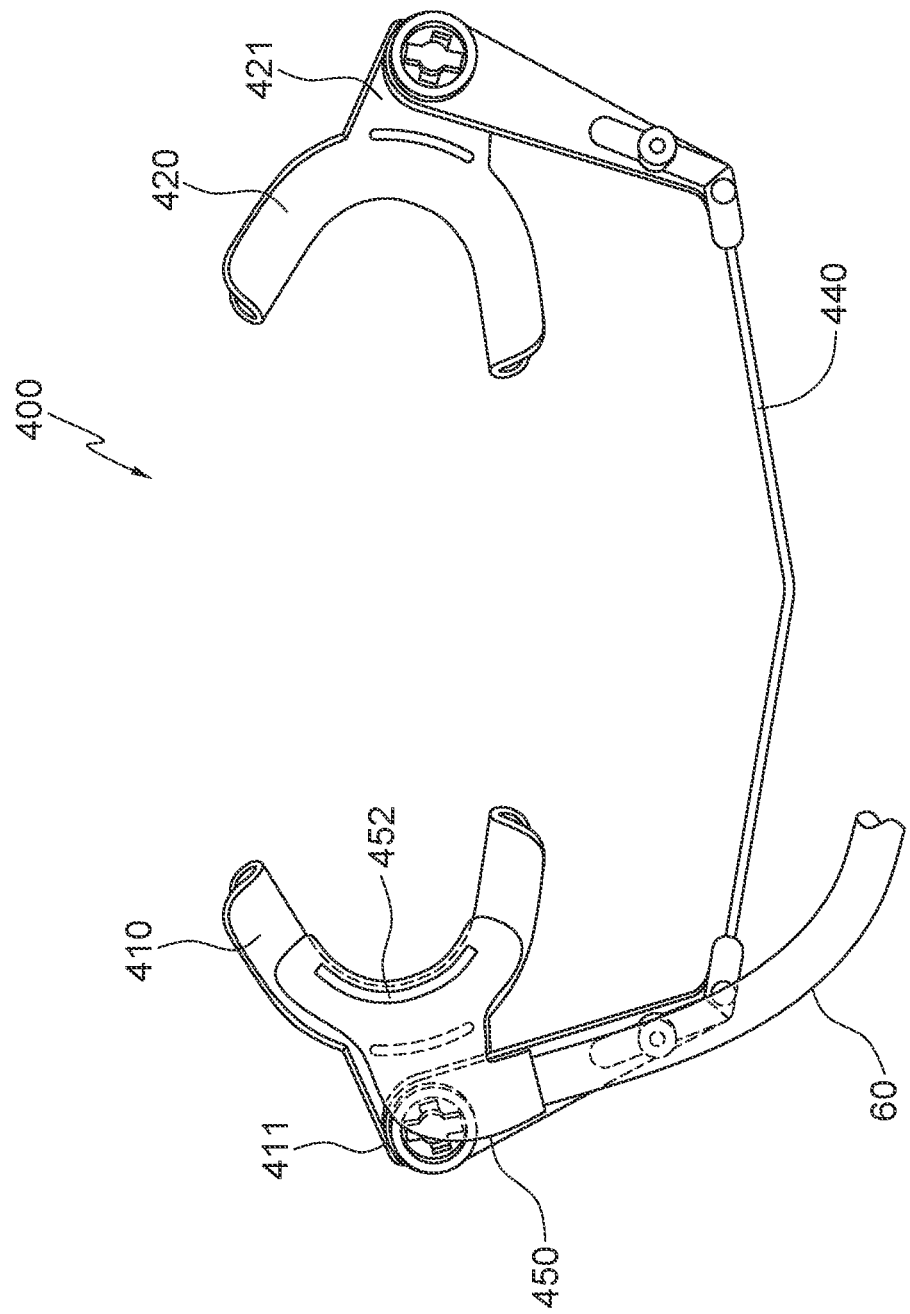
FIG. 18 is front perspective view of an external member with an aerosol reduction assembly.
Figure 19:
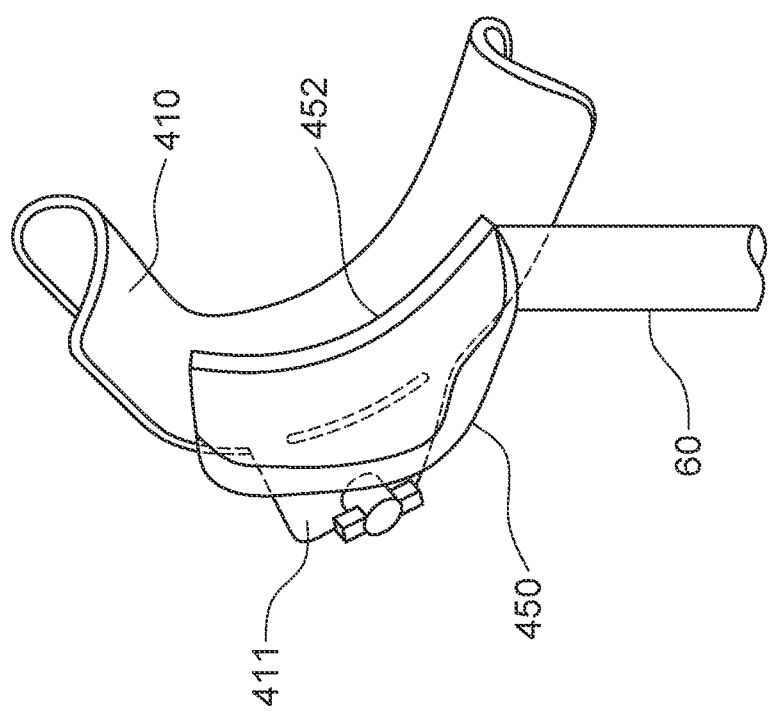
FIG. 19 is a perspective view of a lip retractor of the external member shown in FIG. 18.
Figure 20:
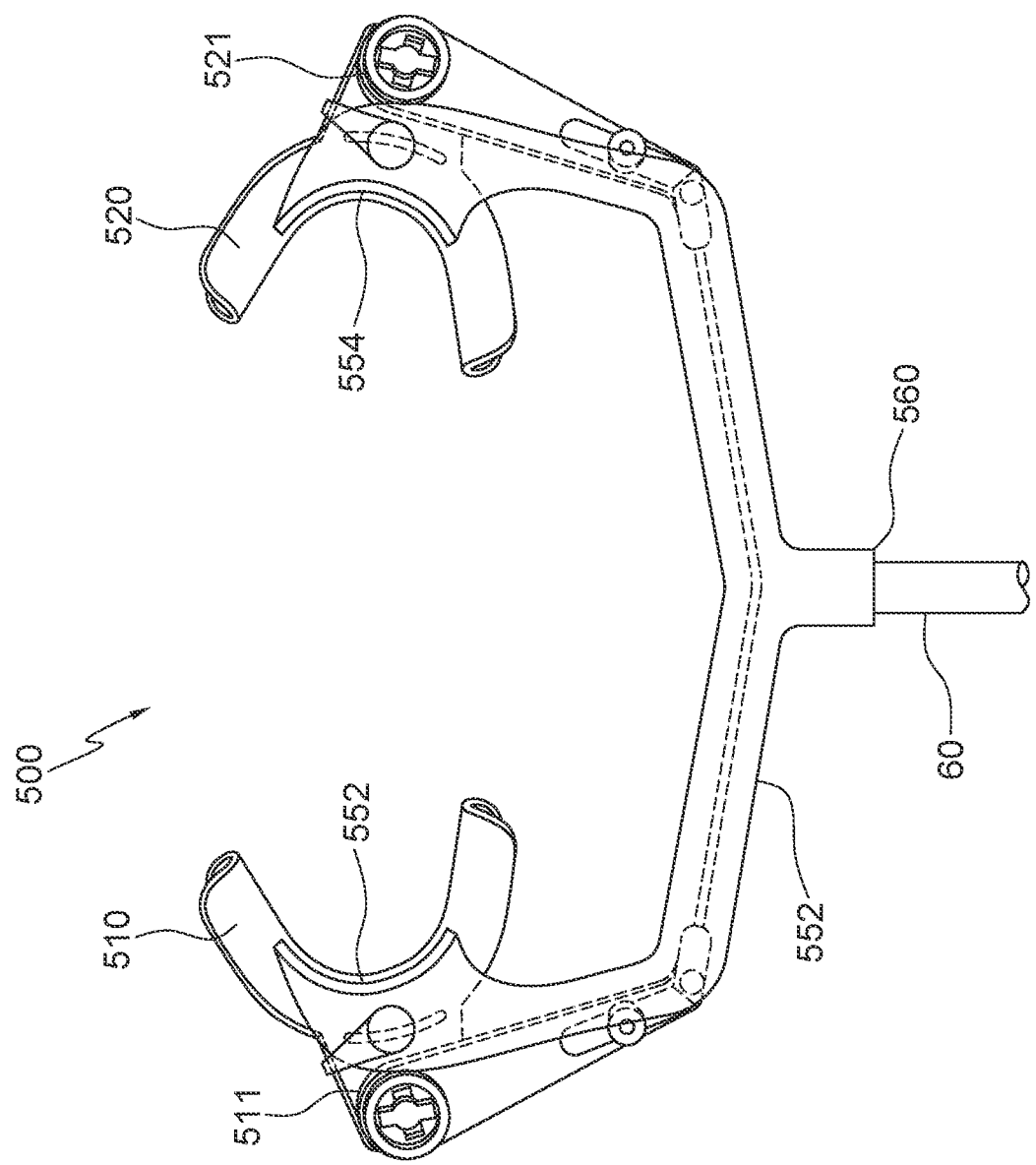
FIG. 20 is a front perspective view of an external member with an aerosol reduction assembly in a further aspect.

FIG. 18 shows an external member 400 in a further aspect with provisions for aerosol reduction and FIG. 19 shows a first lip retractor 410 on the external member 400 with an aerosol reduction assembly 450. When performing dental procedures on a patient the tools and instruments used in the patient's mouth, as well as the patent breathing, can create "spray" that exits the patient's mouth towards the person performing the dental procedures. Not only do these aerosols contain water, which is relatively harmless, but they also can contain saliva, blood and even viruses. To reduce the exposure of the person performing the dental procedure and others in the surrounding area, aerosol reduction is often desirable.

External member 400 is similar to external member 100 in that it contains a first lip retractor 410, a second lip retractor 420, a first retractor flange 411, a second retractor flange 421, and a flexible resilient member 440. However, unlike external member 100, external member 400 has an aerosol reduction assembly 450 for reducing the amount of aerosols that are ejected from a patient's mouth.

The aerosol reduction assembly 450 can have a hollow body with a wide, thin opening 452 directed towards the patient's open mouth and a tubing connector 454 to attach to tubing 60 that can be connected to a suction source. When the suction source is turned on, the suction created in the hollow body of the aerosol reduction assembly 450 can cause suction through the opening 452, sucking airborne aerosols exiting the patient's open mouth into the aerosol reduction assembly 450

The aerosol reduction assembly 450 can be removably attachable to the first lip retractor 410 so that the aerosol reduction assembly 450 can be attached to the external member 400 when desired to control aerosols and then removed so the external member 400 can be used without aerosol reduction when desired.

FIG. 21 is an external member 500 with aerosol reduction in a further aspect. Unlike the external member 400 where suction for aerosol is provided on the first lip retractor 410 sucking aerosols towards the first lip retractor 410 in a single direction, the external member 500 creates suction in two directions to potentially reduce aerosols even more than the external member 400 and the aerosol reduction member 450.

External member 500 can have a first lip retractor 510, a second lip retractor 520, a first retractor flange 511, and a second retractor flange 521, and a flexible resilient member 440. However, unlike external member 400, external member 500 has an aerosol reduction assembly 550 that has a wide, thin first opening 552 provided on the first lip retractor 510 directed toward the opening between the first lip retractor 510 and the second lip retractor 520 and a wide, thin second opening 554 provided on the second lip retractor 520 directed towards the opening between the first lip retractor 510 and the second lip retractor 520.

The aerosol reduction assembly 550 can have a hollow body 560 that acts as a biasing member to force the first lip retractor 510 and the second lip retractor 520 outwards against the lips of a patient, performing the function as the flexible resilient member 440 in the external member 400. The hollow body of the aerosol reduction assembly 550 can also have a tubing connector 560 for connecting tubing 60 so that the aerosol reduction assembly 550 can be connected to a suction source.

When the suction source is turned on, the suction created in the hollow body of the aerosol reduction assembly 550 can cause suction through the first opening 552 and the second opening 552, sucking airborne aerosols exiting the patient's open mouth towards both the first lip retractor 510 and the second lip retractor 520 an into the aerosol reduction assembly 550 when it can be sucked out through the tubing 60 and away.

The foregoing is considered as illustrative only of the principles of the invention. Further, since numerous changes and modifications will readily occur to those skilled in the art, it is not desired to limit the invention to the exact construction and operation shown and described, and accordingly, all such suitable changes or modifications in structure or operation which may be resorted to are intended to fall within the scope of the claimed invention.

What is claimed is:

1. An internal member for an intra-oral appliance comprising:
    a tongue crib defining an interior space sized to accept a tongue of a patient and enclose at least an anterior tip of the tongue of the patient, the tongue crib having an opening in a back end of the tongue crib leading into the interior space;
    a poseable first arm connected at a first end to the back end of the tongue crib; and
    a poseable second arm connected at a first end to the back end of the tongue crib,
    wherein the poseable first arm and the poseable second allow the tongue crib to be moved into a position and held in the position,
    and wherein the poseable first arm and the poseable second arm comprise tubing,
    and wherein the first poseable arm comprises a first side of tubing, and a poseable wire integrated into the first side of tubing, and wherein the second poseable arm comprises a second side of tubing and a poseable wire integrated into the second side of tubing,
    and wherein the poseable wire runs out of the first end of the first side of tubing, into the tongue crib, around a periphery of the tongue crib, out of the tongue crib and into the first end of the second side of tubing.

2. The internal member of claim 1 wherein the poseable wire integrated into the first side of tubing and the poseable wire integrated into the second side of tubing is the same poseable wire.

3. The internal member of claim 2 wherein the poseable wire bridges a gap between an end of the first side of tubing and the tongue crib and a gap between an end of the second side of the tubing and the tongue crib.

4. The internal member of claim 1 further comprising a first sub-lingual aperture provided at an end of the first side of tubing and a second sub-lingual aperture provided at an end of the second side of tubing.

5. The internal member of claim 2 wherein the first sub-lingual aperture is an open end of the first side of tubing and the second sub-lingual aperture is an open end of the second side of tubing.

6. The internal member of claim 1 further comprising a first retro-molar pad aperture provided in a bottom of the first side of tubing where the first side of tubing passes over a retro-molar pad of the patient when the internal member is positioned in a mouth of the patient and a second retro-molar pad aperture provided in a bottom of the second side of tubing where the second side of tubing passes over a retro-molar pad of the patient when the internal member is positioned in the mouth of the patient.

7. The internal member of claim 1 further comprising a channel running through the first arm sized to accept tubing and a channel running through the second arm sized to accept tubing.

8. The internal member of claim 7 further comprising a u-shaped channel provided in a bottom of the tongue crib.

9. An intra-oral appliance comprising:
    an internal member comprising:
        a tongue crib defining an interior space sized to accept a tongue of a patient, the tongue crib having an opening in a back end of the tongue crib leading into the interior space;
        a poseable first arm connected at a first end to the back end of the tongue crib; and
        a poseable second arm connected at a first end to the back end of the tongue crib,
        wherein the poseable first arm and the poseable second allow the tongue crib to be moved into a position and held in the position,
        and wherein the poseable first arm and the poseable second arm comprise tubing; and
    an external member comprising:
        a first lip retractor having a generally arcuate shape, an inner surface, and an outer surface having an open channel with a substantially semi-circular cross-section;
        a second lip retractor having a generally arcuate shape, an inner surface, and an outer surface having an open channel with a substantially semi-circular cross-section;
        a first retractor flange connected to the first lip retractor at a front end of the first lip retractor and extending outwards from the outer surface of the first lip retractor;
        a second retractor flange connected to the second lip retractor at a front end of the second lip retractor and extending outwards from the outer surface of the second lip retractor;
        a first wing member attached to the first lip retractor and extending backwards from the inner surface of the first lip retractor;
        a second wing member attached to the second lip retractor and extending backwards from the inner surface of the second lip retractor;
        a flexible resilient member connected between the first retractor flange and the second retractor flange, the flexible resilient member biasing the first lip retractor and the second lip retractor apart; and
        connectors attachable to the tubing of the first arm and the tubing of the_second arm of the internal member, the connectors comprising:
            a first connector having an aperture passing through the first retractor flange sized to accept the first poseable arm; and, a second connector having an aperture passing through the second retractor flange sized to accept the second poseable arm.

10. The intra-oral appliance of claim 9 wherein the first poseable arm of the internal member comprises a first side of tubing, and a poseable wire integrated into the first side of tubing, and wherein the second poseable arm of the internal member comprises a second side of tubing and a poseable wire integrated into the second side of tubing.

11. The intra-oral appliance of claim 9 wherein the aperture of the first connector has an opening at a top of the first retractor flange and the aperture of the second connector has an opening at a top of the second retractor.

* * * * *